United States Patent
Hsu (10) Patent No.: US 6,576,109 B1
(45) Date of Patent: Jun. 10, 2003

(54) GEL TRAY STRUCTURE OF AN ELECTROPHORESIS TROUGH

(75) Inventor: Yi-Hua Hsu, Taipei (TW)

(73) Assignee: Wealtec Enterprise Co., Ltd., Taipei (TW)

(*) Notice: Subject to any disclaimer, the term of this patent is extended or adjusted under 35 U.S.C. 154(b) by 260 days.

(21) Appl. No.: 09/670,553

(22) Filed: Sep. 27, 2000

(51) Int. Cl.[7] .................... C02F 1/40; C02F 11/00; C25B 11/00; C25B 13/00; C25B 9/00; G01N 27/27; G01N 27/403; G01N 27/453
(52) U.S. Cl. ............................................ 204/616
(58) Field of Search .................................. 204/616

(56) References Cited

U.S. PATENT DOCUMENTS

| | | | | |
|---|---|---|---|---|
| 4,828,669 A | * | 5/1989 | Hellman, Jr. | 204/618 |
| 5,632,877 A | * | 5/1997 | Van Atta | 204/467 |
| 6,110,340 A | * | 8/2000 | Lau et al. | 204/467 |
| 6,162,342 A | * | 12/2000 | Perez et al. | 204/467 |
| 6,179,980 B1 | * | 1/2001 | Aksberg | 204/616 |
| 6,436,262 B1 | * | 8/2002 | Perez | 204/466 |

* cited by examiner

Primary Examiner—Mark L. Bell
Assistant Examiner—Jennine M Brown
(74) Attorney, Agent, or Firm—Bacon & Thomas (57) ABSTRACT

A gel tray to be inserted into an electrophoresis trough having stop members and a stop plate as well as engaging members to securely abut the plate to the trough body. This feature allows for leak free gel casting. To adapt for electrophoresis, just remove the stop members for a fast and convenient way to consolidate steps when compared to conventional techniques.

7 Claims, 11 Drawing Sheets

GEL TRAY STRUCTURE OF AN ELECTROPHORESIS TROUGH

BACKGROUND OF THE INVENTION

1. Field of the Invention

The present invention is related to improvement of the structure of gel tray of a horizontal electrophoresis trough used for biologic experiments, and especially to an improved gel tray which renders the process of consolidation of gel fast and convenient against the defects of having the necessity to repeat manufacturing processes resided in conventional techniques.

Horizontal electrophoresis troughs are designed for separation and analysis in DNA (deoxyribonucleic acid) and RNA (ribonucleic acid) in biotechnology, this is based on the principle that electric current drives molecules to move in gel formed from a kind of porous material, and the DNA and RNA are separated by difference of the electric load of the ionic elements and sizes of the molecules respectively of the DNA and RNA themselves. This occupies an extreme important position in the application of the basic theory of biotechnology.

Figure 1:
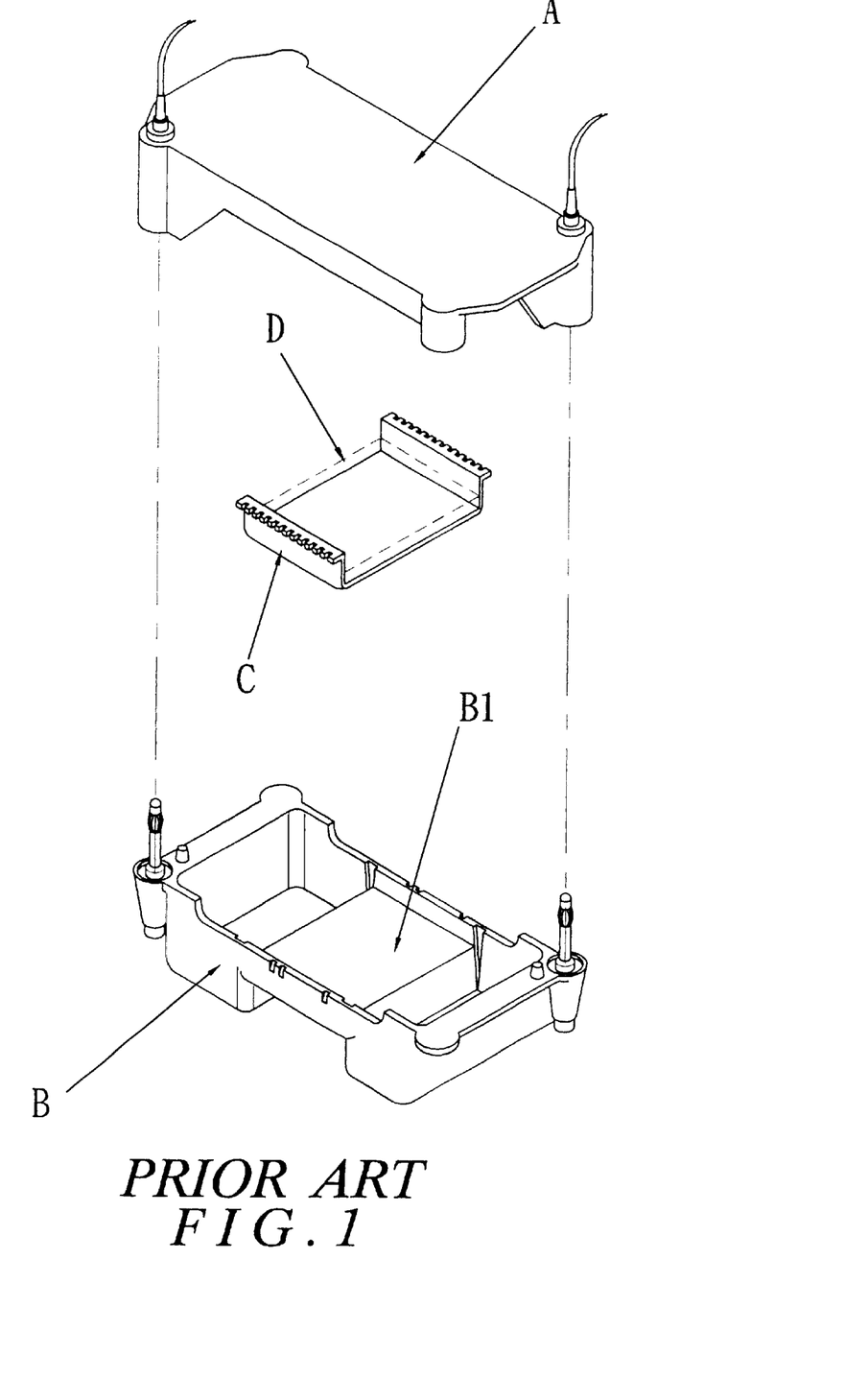
FIG. 1 is an analytic perspective view of an electrophoresis trough and a gel tray.

As shown in FIG. 1, an electrophoresis trough is comprised mainly of an upper lid A, a lower trough body B and a gel tray C, wherein, the upper lid A and the lower trough body B are provided on the front and rear ends thereof with electrode members, the lower trough body B is in the form of a vessel to receive therein buffer solution for an experiment, a platform B1 is provided centrally of the lower trough body B to support the gel tray C. Two walls are provided laterally of the gel tray C which is opened on the front and rear sides thereof. When the gel tray C is provided therein with pre-consolidated gel D, and a solution sample for analysis and test is placed in a sample hole on the gel D in the lower trough body B, then the electrode members are electrically connected to drive the molecules in the sample from the negative electrode toward the positive electrode, in order to separate molecules of different natures.

In the above process, the liquid gel D must be consolidated into a porous solid state in advance for proceeding of the experiment, and the front and rear sides of the pre-consolidated gel D must be kept plane in order to get correct conclusion of the experiment. Therefore, the preference conditions for analysis and test of the experiment are to find a way to consolidate the gel in the gel tray and to keep it intact in the electrophoresis trough.

2. Description of the Prior Art

A method for consolidation of gel in the early period was to use sterilized tapes to seal the opened front and rear ends of a gel tray C, and then to cast liquid gel therein; the sterilized tapes were torn off after consolidation of the gel.

Such method using sterilized tapes is simple and convenient, however, it is disadvantageous in that sterilized tapes are soft tapes, pressure created by the cast liquid gel will spread the sterilized tapes outwardly to form arciform rims on the solidified gel and to make leakage at the gaps resulted at the junctions of the sterilized tapes and the gel tray. Thereby, rough edges are generated at the front and rear ends of the consolidated gel, this influences quality of samples in the experiment, an operator even needs to repeat for several times or makes once for all many spare consolidated gels in order to get a gel perfectly manufactured. This is time and spirit consumptive. Besides, the gel leakage by capillarity will make untidy of the table surface in a lab. And more, the sterilized tapes are discarded after use; they cannot be repeatedly used and thus are uneconomic.

Figure 2:
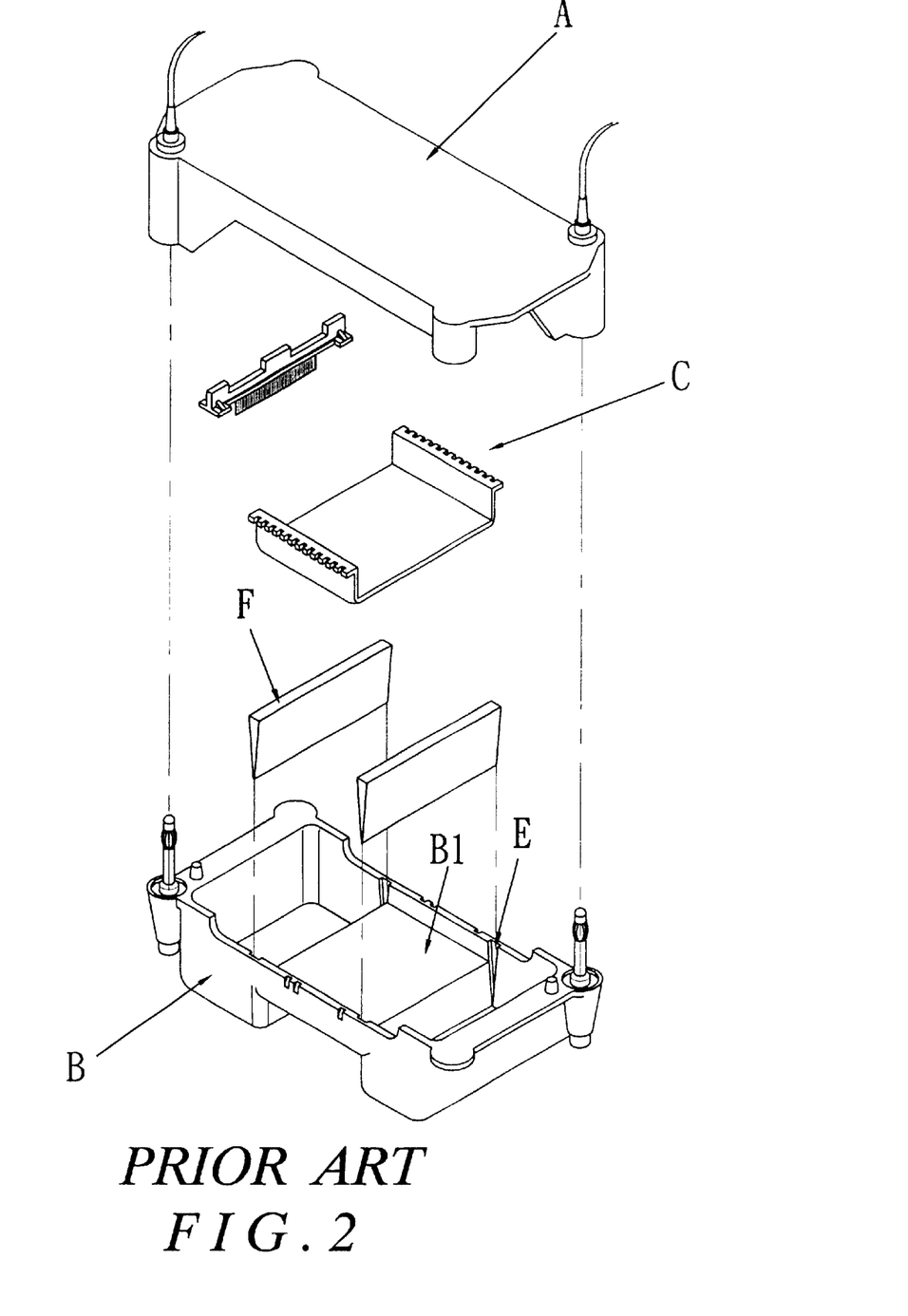
FIG. 2 is an analytic perspective view showing consolidation of gel in the electrophoresis trough mounted with stop plates.

As shown in FIG. 2 which shows a second conventional method, wherein, the gel tray C is directly placed under the platform B1 of the lower trough body B, and the lower trough body B is provided at the locations on the lateral sides thereof near by the front and rear ends of the gel tray C with a plurality of vertical "V" shaped grooves E for inserting therein stop plates F. The stop plates F form barrels inside of the front and rear ends of the gel tray C. Thereby, after consolidation of the cast liquid gel, the stop plates F can be removed, and manufacturing of the gel can be completed.

Such method has the advantage that after removing of the stop plates F, if the consolidated gel is perfect, it can be used directly for the experiment, and can be repeatedly used. However, it has the disadvantages that, tightness of closing of the stop plates F and the grooves E is insufficient, leakage still exists; and consolidation of the cast liquid gel directly in the lower trough body B results inability of making many spare consolidated gels (unless there are many expensive electrophoresis troughs). If the gel is damaged, it must be manufactured again from the beginning and must wait again for consolidation; this is troublesome and time consuming. And more, after consolidation, the rims of the consolidated gels will be attached to the stop plates F; hence when the stop plates F are removed by lifting upwardly, the consolidated gels may be damaged. Further, by the fact that the objects for the gel tray C in the experiment may be varied, widths of the front and rear ends of the gel tray C include at least two kinds, each gel tray C can only be used for a specific electrophoresis trough, i.e., at least two electrophoresis troughs of different specifications must be provided for a lab, this is surely uneconomic.

Figure 3:
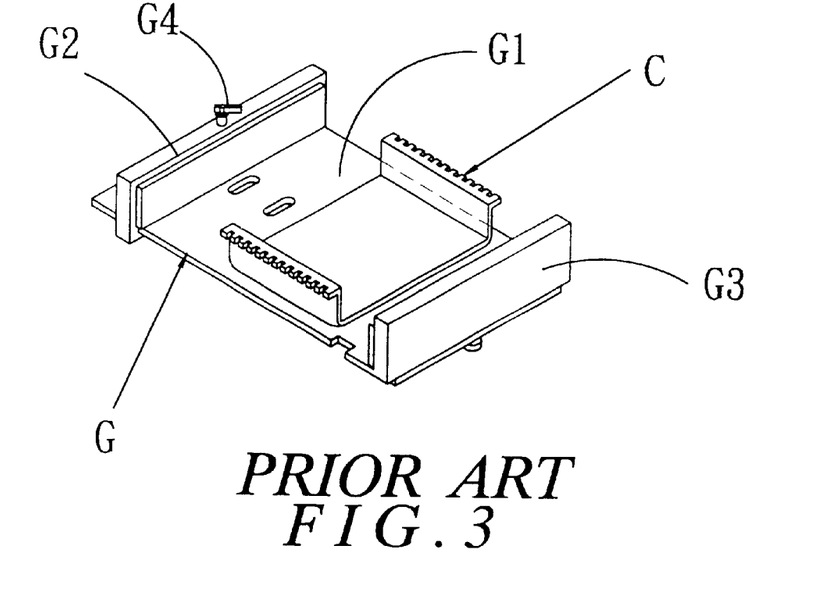
FIG. 3 is a perspective view showing a conventional gel tray on an assisting auxiliary seat.
Figure 4:
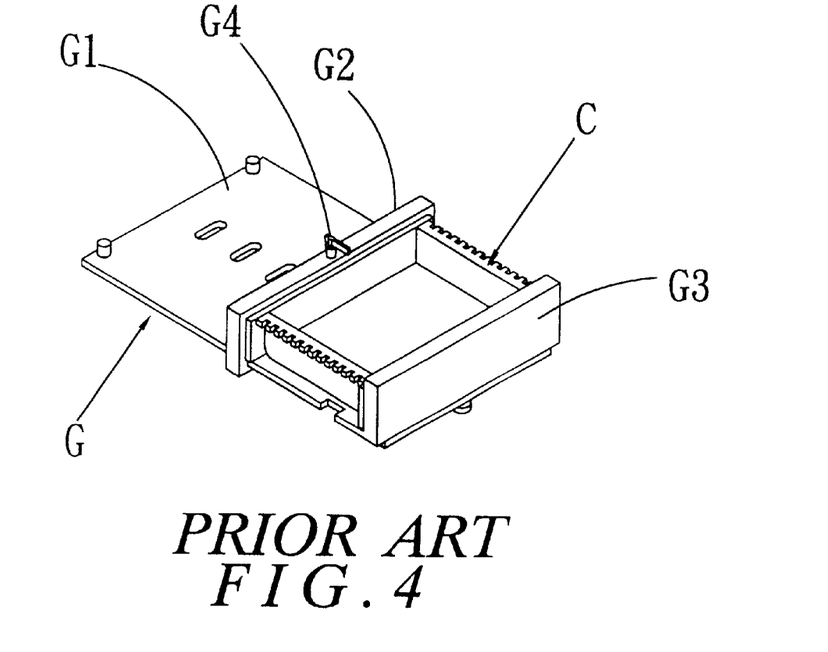
FIG. 4 is a perspective views showing the conventional gel tray with an assisting auxiliary seat is used for consolidation of gel.

As shown in FIGS. 3 and 4, they show a third known technique, wherein, an auxiliary seat G is used to assist a gel tray C for gel consolidation, the auxiliary seat G is comprised of a base G1, a movable front stop plate G2 and a fixed rear stop plate G3. The gel tray C is placed on the base G1 with the rear end thereof being abutted against the fixed rear stop plate G3. Now the movable front stop plate G2 can be adjusted horizontally to close to the front end of the gel tray C, a rotary knob G4 can be screwed tight and then the front and rear ends of the gel tray C are sealed in order to proceed gel consolidation. The rotary knob G4 is unscrewed after gel consolidation to allow moving outwardly of the movable front stop plate G2, thus manufacturing is completed.

Such method using the auxiliary seat G to assist the gel tray C has a defect of being more trouble in operation, and cost of the auxiliary seat G is more expensive. While it is quite safe to release the consolidated gel by moving outwardly of the movable front stop plate G2 without damaging the consolidated gel, this can be an important reference.

Figure 5:
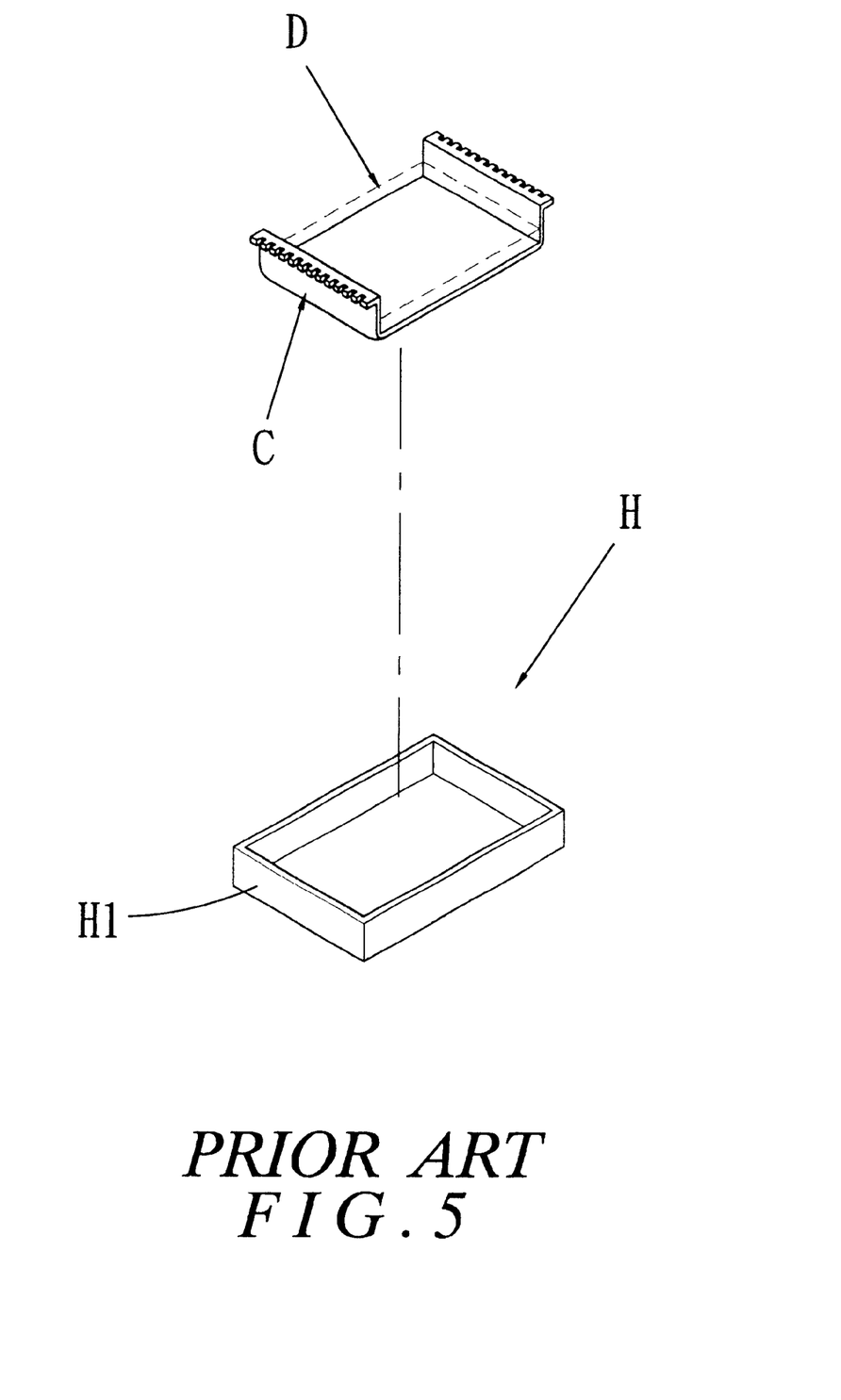
FIG. 5 is an analytic perspective view showing a gel tray and a container in a conventional technique are under the process of consolidation of gel.

As shown in FIG. 5 which shows a fourth conventional method, wherein, a gel tray C is directly placed in a container H, the gel tray C is sealed by surrounding plates H1, liquid gel D is cast into the gel tray C and is consolidated, then the gel tray C can be taken out. Such a conventional structure can be very convenient for use; however, it has the same defect as that of the structure shown in FIG. 2, i.e., the consolidated gel D is subjected to damage.

SUMMARY OF THE INVENTION

The inventor of the present invention developed the improved structure of gel tray for an electrophoresis trough based on his specific experience of years in manufacturing as well as selling biologic experimental instruments and after synthesizing the advantages and disadvantages of the conventional techniques. With this structure, the gel tray can complete gel consolidation faster, more convenient and more economic.

In particular, the gel tray of the present invention is comprised mainly of a body and a front and a rear stop member, wherein, the body can be placed in an electrophoresis trough. Two side wall-plates on the bottom plane plate of the gel tray are extended vertically upwardly and provided with a plurality of recesses; the front and rear ends of the bottom plane plate are opened. The above stated stop members are further respectively provided with a stop plate, and are respectively assembled together with an engaging member and a lever latch. When the front and rear stop members are respectively placed on the front and rear ends of the tray body with the stop plates thereon, they can be engaged in the recesses on the side wall-plates by moving the lever latches on the engaging members. So that the stop plates tightly abut against the front and rear ends of the tray body, the surrounding walls of the tray body thus are formed in a sealing state for casting therein liquid gel. After consolidation of the gel, the tray body can be released from engaging of the side wall-plates again by moving of the lever latches to move the engaging members. The stop members thereby can be detached without damaging the front and rear end surfaces of the consolidated gel.

The present invention has the following advantages structurally:
1. Mounting and detaching of the front and rear stop members are very fast and convenient; they are operationally easy and convenient for use.
2. When in detaching the stop members after consolidation of the gel, the stop plates are moved away from the gel horizontally, thereby, the front and rear end surfaces of the consolidated gel will not be damaged.
3. The front and rear stop members of the present invention can suit gel trays of various widths, there is no need to purchase another electrophoresis trough to suit another gel tray.
4. Cost of production of the stop members is inexpensive; a user is not necessarily to purchase them with overly expensive prices.

The present invention will be apparent in its particular structure and function after reading the detailed description of the preferred embodiment thereof in reference to the accompanying drawings.

DETAILED DESCRIPTION OF THE PREFERRED EMBODIMENT

Figure 6:
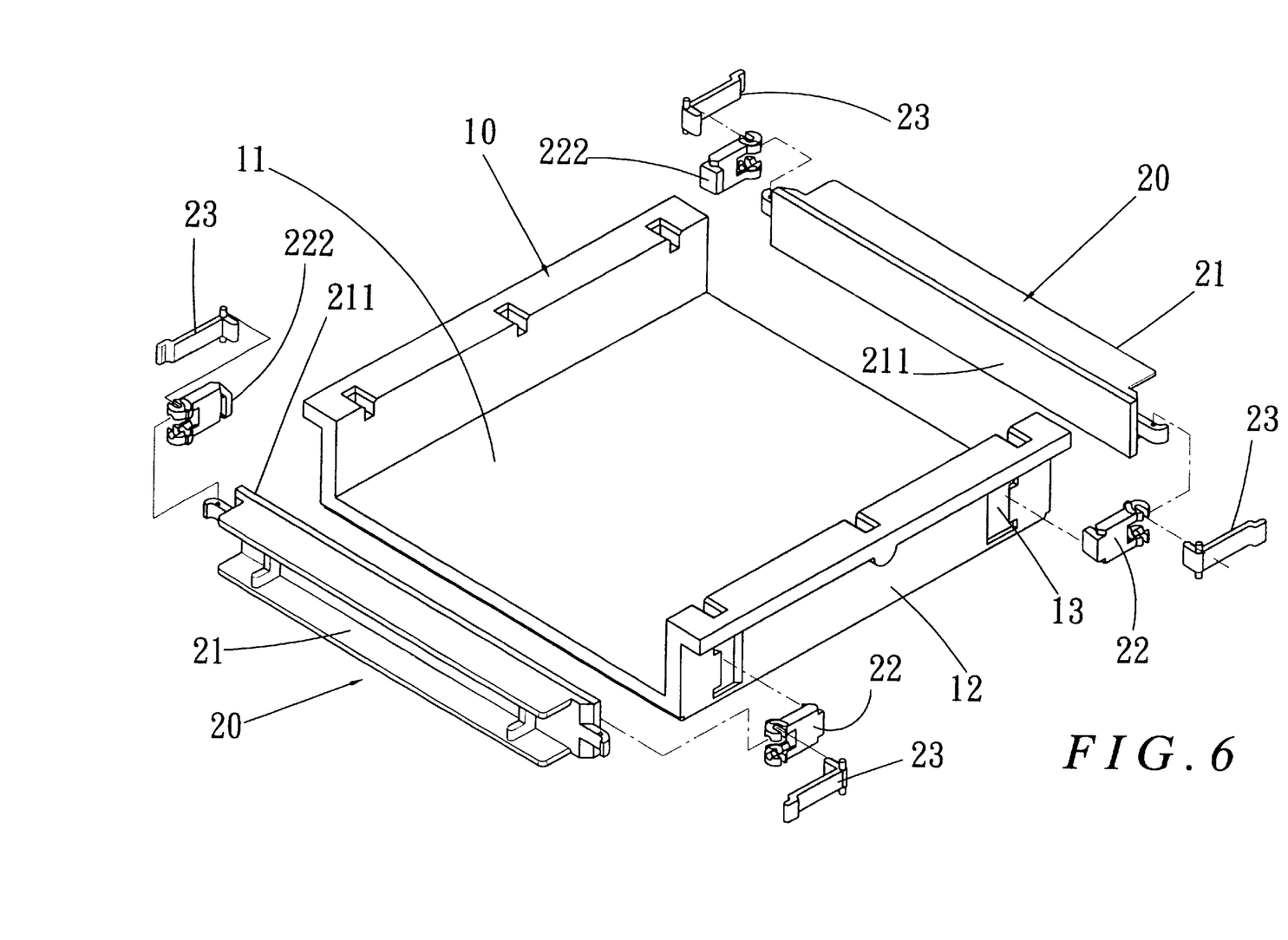
FIG. 6 is an analytic perspective view of a gel tray of the present invention.
Figure 7:
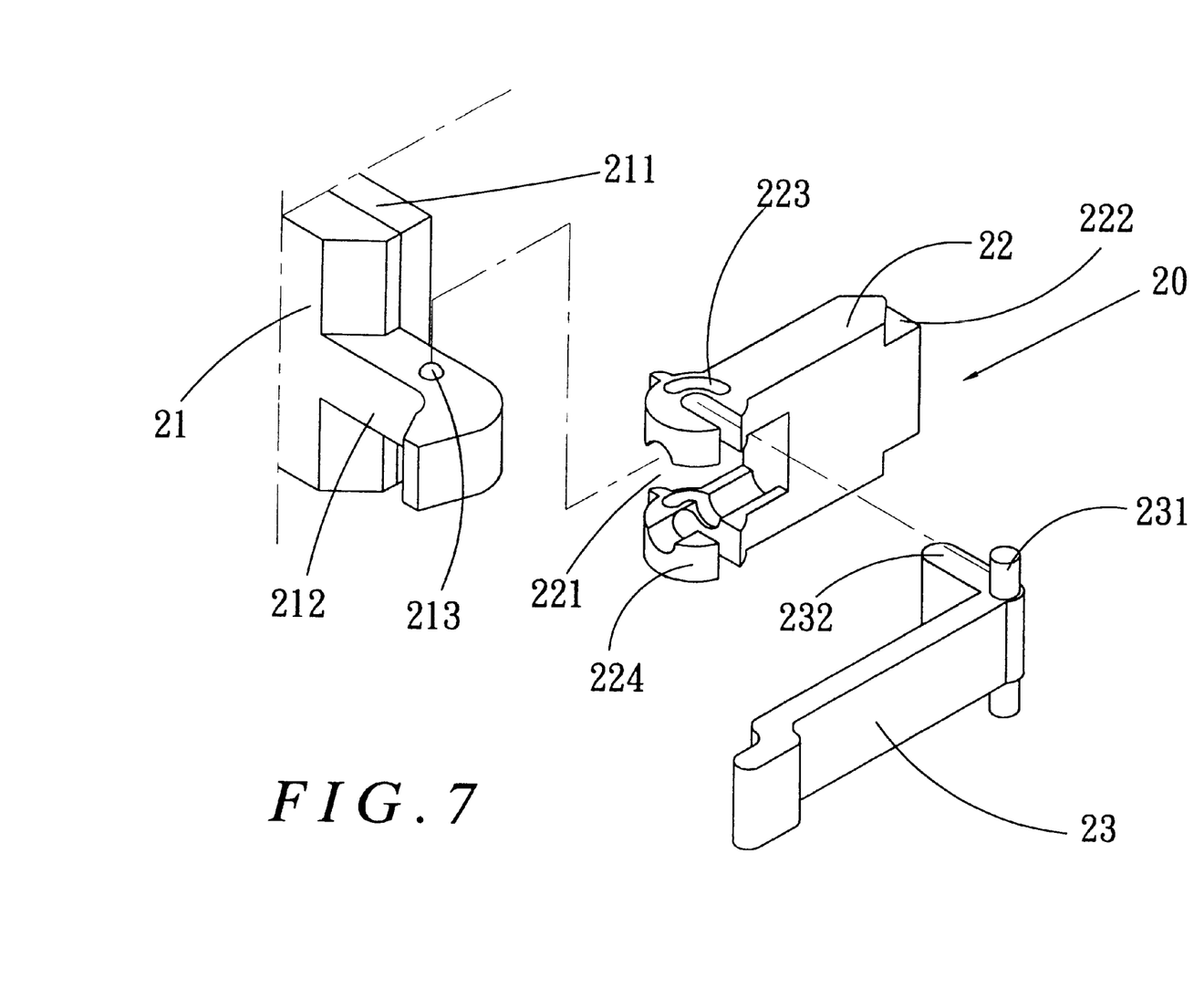
FIG. 7 is a partially enlarged perspective view of FIG. 5.

Referring firstly to FIGS. 6 and 7, the gel tray of the electrophoresis trough of the present invention is comprised structurally mainly of a tray body 10 and a front and a rear stop member 20.

Wherein, the tray body 10 can be placed in the electrophoresis trough. Two side wall-plates 12 on a bottom plane plate 11 of the tray body 10 are extended vertically upwardly and are provided with a plurality of recesses 13, the front and rear ends of the bottom plane plate 11 are opened.

The stop members 20 are further provided each with a stop plate 21, and with an engaging member 22 and a lever latch 23 respectively assembled on one side and the other side thereof. When the front and rear stop members 20 are respectively placed on the front and rear ends of the tray body 10 with the stop plates 21 thereon, the surrounding walls of the tray body 10 thus are formed in a sealing state, hooks 222 provided on the engaging members 22 can be engaged in the recesses 13 on the side wall-plate 12 by moving the lever latches 23 on the engaging members 22. So that the stop plates 21 tightly abut against the front and rear ends of the tray body 10 for casting therein liquid gel. After consolidation of the gel, the tray body 10 can be released from engaging of the side wall-plates 12 again by moving of the lever latches 23 to move the engaging members 22. The stop members 20 thereby can be detached without damaging the front and rear end surfaces of the consolidated gel.

Referring to FIG. 7, the structure features of the stop plates 21, the engaging members 22 and the lever latches 23 of the stop members are as below:

The stop plates 21 are straight and plane, and are provided each on the inner side thereof facing to the front and rear ends respectively of the tray body with a leakage-proof elastic rubber cushion 211. The stop plates 21 are provided each on both ends thereof with a connecting piece 212 having a bending end, the connecting piece 212 is provided on the top and bottom thereof each with a protruding point 213.

The engaging members 22 each is mounted on the connecting piece 212 of a stop plate 21 and is provided on one end thereof with a notch 221 and on the other end thereof with a hook 222. Wherein, the notch 221 is to clamp on the connecting piece 212 in contact with the protruding points 213 of the connecting piece 212. The engaging members 22 each is further provided with a guide groove 223 for insertion of the protruding points 213. The guide groove 223 includes two sections, one is straight; the other is arciform. When the engaging member 22 is connected to a connecting piece 212, the guide groove 223 slides on the protruding points 213 to allow the connecting piece 212 to move to and fro or in a mode of swaying in an arc. And a pivot connecting seat 224 is provided just outside of the notch 221.

The lever latches 23 each has a pivot axle 231 for connecting to the pivot connecting seat 224 of the engaging member 22, in order that the lever latch 23 can be swiveled about the pivot connecting seat 224. The lever latch 23 has a pushing panel 232 corresponding in operation to the bending end on the connecting piece 212.

Figure 8:
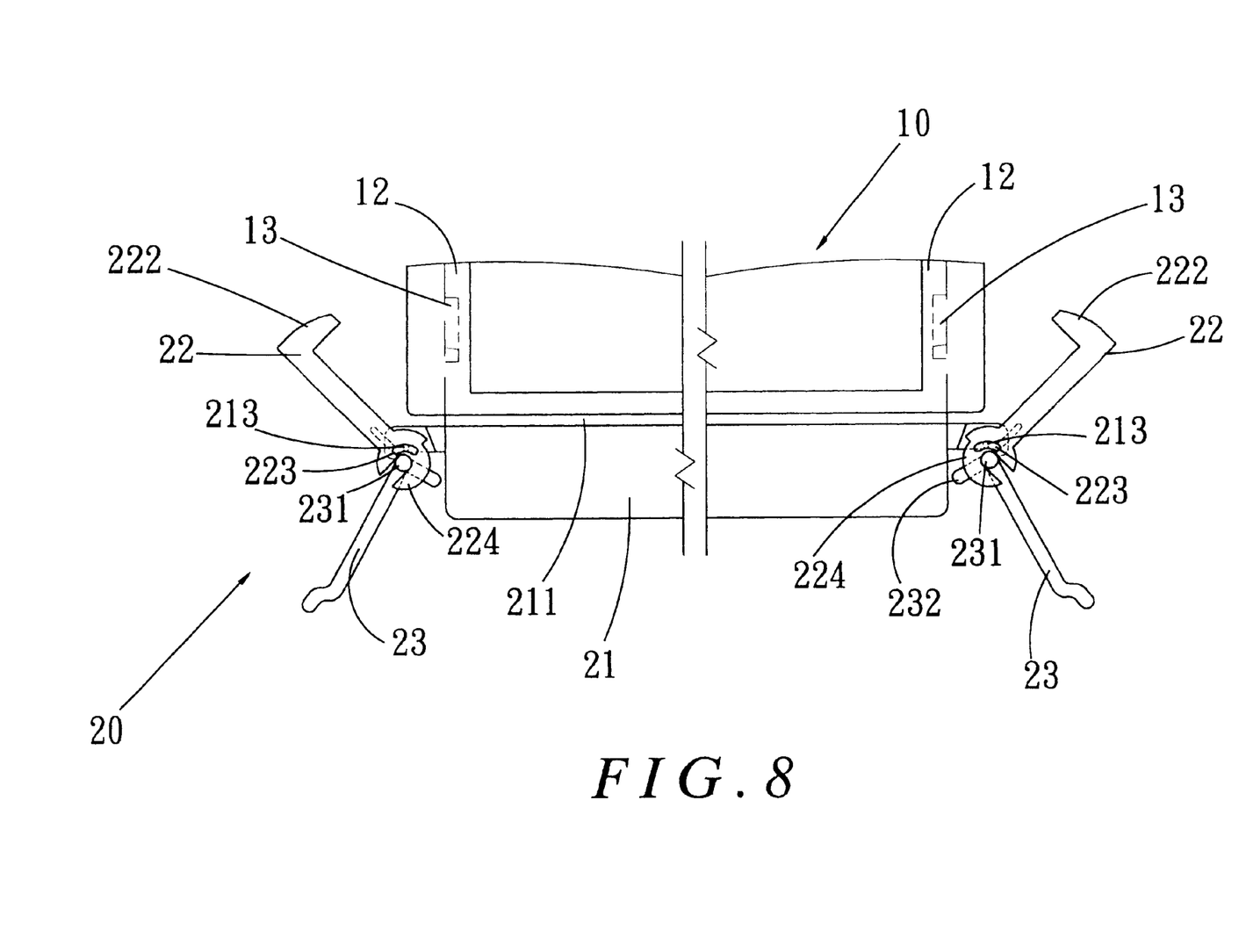
FIG. 8 is a top view showing the tray body and stop members of the gel tray of the present invention before being assembled.

Referring to FIG. 8 which is a top view showing the tray body 10 and the stop members 20 on the gel tray of the present invention before being assembled, wherein, the stop members 20 are respectively placed on the front and rear ends of the tray body 10, the stop plates 21 of the stop members 20 are located now respectively at the front and rear ends of the tray body 10, the engaging members 22 at both sides of each of the stop plates 21 are in the state of opening outwardly, and the lever latches 23 has not moved the engaging members 22 yet.

Figure 9:
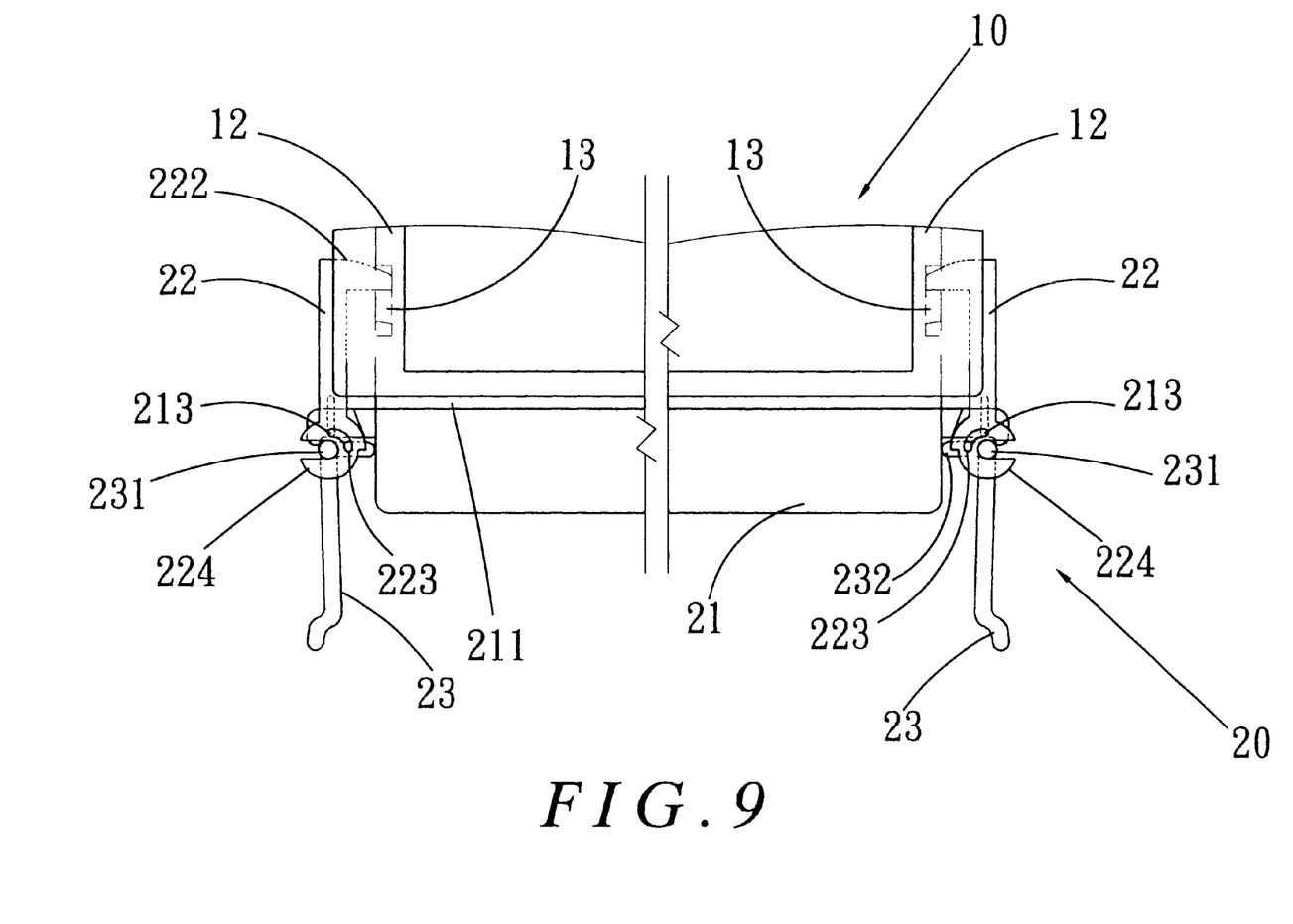
FIG. 9 is a schematic view showing assembling of the tray body and the stop members of the gel tray of the present invention.

Referring to FIG. 9 which is a schematic view showing assembling of the tray body 10 and the stop members 20 of the gel tray of the present invention, wherein, the stop plates 21 of the stop members 20 at the front and rear ends are abutted respectively against the front and rear ends of the tray body 10, the surrounding walls of the tray body 10 thus are formed in a sealing state. Then the engaging members 22 are moved toward the two side wall-plates 12 of the tray body 10 each in a mode of displacement in an arciform path to make hooks 222 on the engaging members 22 engaged in the recesses 13 on the side wall-plates 12. Moving of the engaging members 22 in arciform paths can be effected by cooperation of the guide groove 223 with the protruding points 213.

Figure 10:
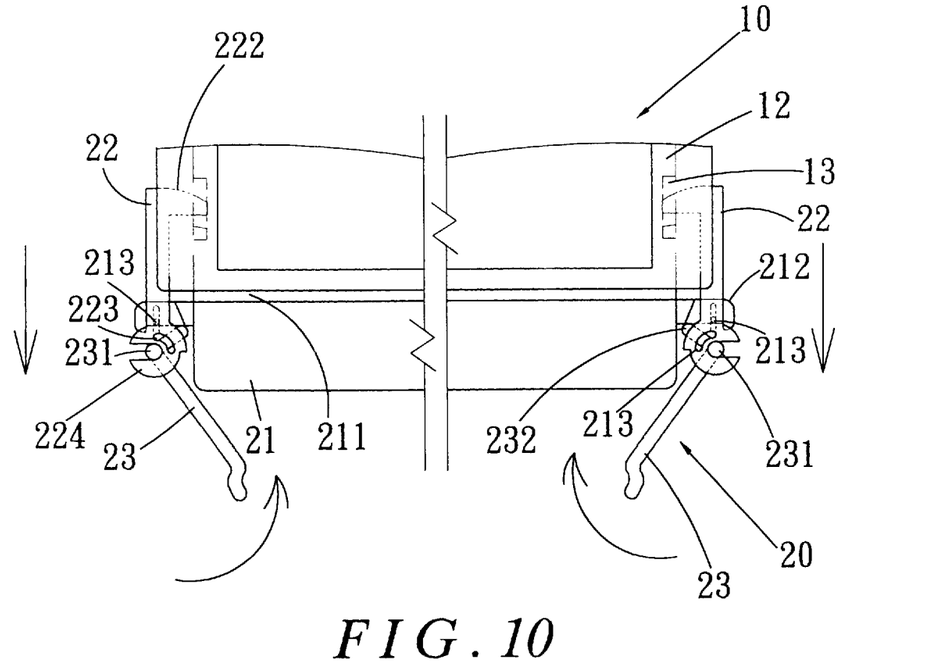
FIG. 10 is another schematic view showing assembling of the tray body and the stop members of the gel tray of the present invention.

Referring to FIG. 10 which is another schematic view showing assembling of the tray body 10 and the stop members 20 of the gel tray of the present invention, wherein, after the hooks 222 on the engaging members 22 are placed into the recesses 13 on the side wall-plates 12, the lever latches 23 are moved to swivel about the pivot connecting seat 224, the pushing panels 232 of the lever latches 23 are abutted against the bending ends on the connecting pieces 212 to exert an action force to move the engaging members 22 and the hooks 222 downwardly in the drawing to make them slide. During sliding, the protruding points 213 are located in the straight sections of the guide grooves 223, so that the engaging members 22 and the hooks 222 thereof slide downwardly in a straight line.

Figure 11:
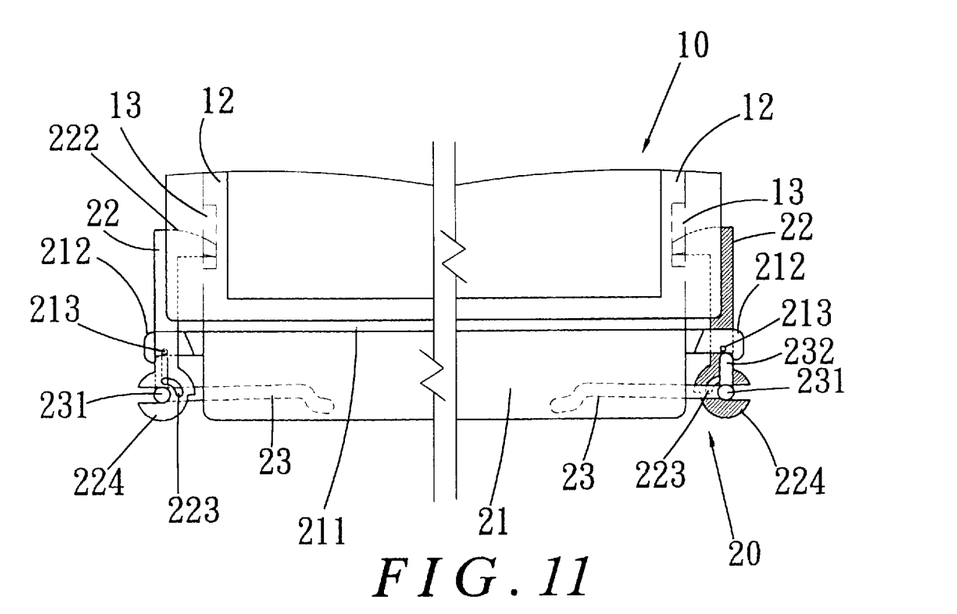
FIG. 11 is a top view showing completing of assembling of the tray body and the stop members of the gel tray of the present invention.

Referring to FIG. 11 which is a top view showing completing of assembling of the tray body and the stop members, wherein, before the lever latches 23 are moved to the terminal positions of their strokes, the hooks 222 on the engaging members 22 are moved downwardly and are abutted against the recesses 13 on the side wall-plates 12, thereby the stop plates 21 get close to the tray body 10 and press the latter. When the lever latches 23 are moved to the terminal positions of their strokes, the leakage-proof cushions 211 of the stop plates 21 provided with elasticity are tightly abutted against the front and rear ends of the tray body 10 and the side wall-plates 12, so that the surrounding walls of the tray body 10 are formed in a sealing state for casting therein liquid gel for consolidation. No liquid gel will leak out.

Summarily, from the above structural connecting relationship of the present invention stated in reference to FIGS. 6 to 11, when a user assembles the tray body 10 and the stop members 20, the stop members 20 need only to be placed respectively on the front and rear ends of the tray body 10 (only the front end is shown in the drawings by virtue that the front and rear ends are identical to each other only with opposite orientations mutually) to make the stop plates 21 block the front and rear ends of the tray body 10, then the engaging members 22 and the hooks 222 abut against the recesses 13 on the side wall-plates 12, and move the lever latches 23 to make the stop plates 21 tightly abut against the ends of the tray body 10 to complete connection. This is very convenient and quick in operation.

One thing worth mentioning, after consolidation of the liquid gel in the tray body 10, and when it is to detach the stop members 20 to proceed the experiment, the leakage-proof cushions 211 provided with elasticity and abutted tightly against the tray body 10 and the side wall-plates 12 will give an elastic force, by moving the lever latches 23 to release the hooks 222 on the engaging members 22 from the recesses 13, to move the stop plates 21 away from the tray body 10 outwardly. Thereby, the stop plates 21 during detachment will not abrade the consolidated gel, and the front and rear end surfaces of the consolidated gel can be kept intact.

Figure 12:
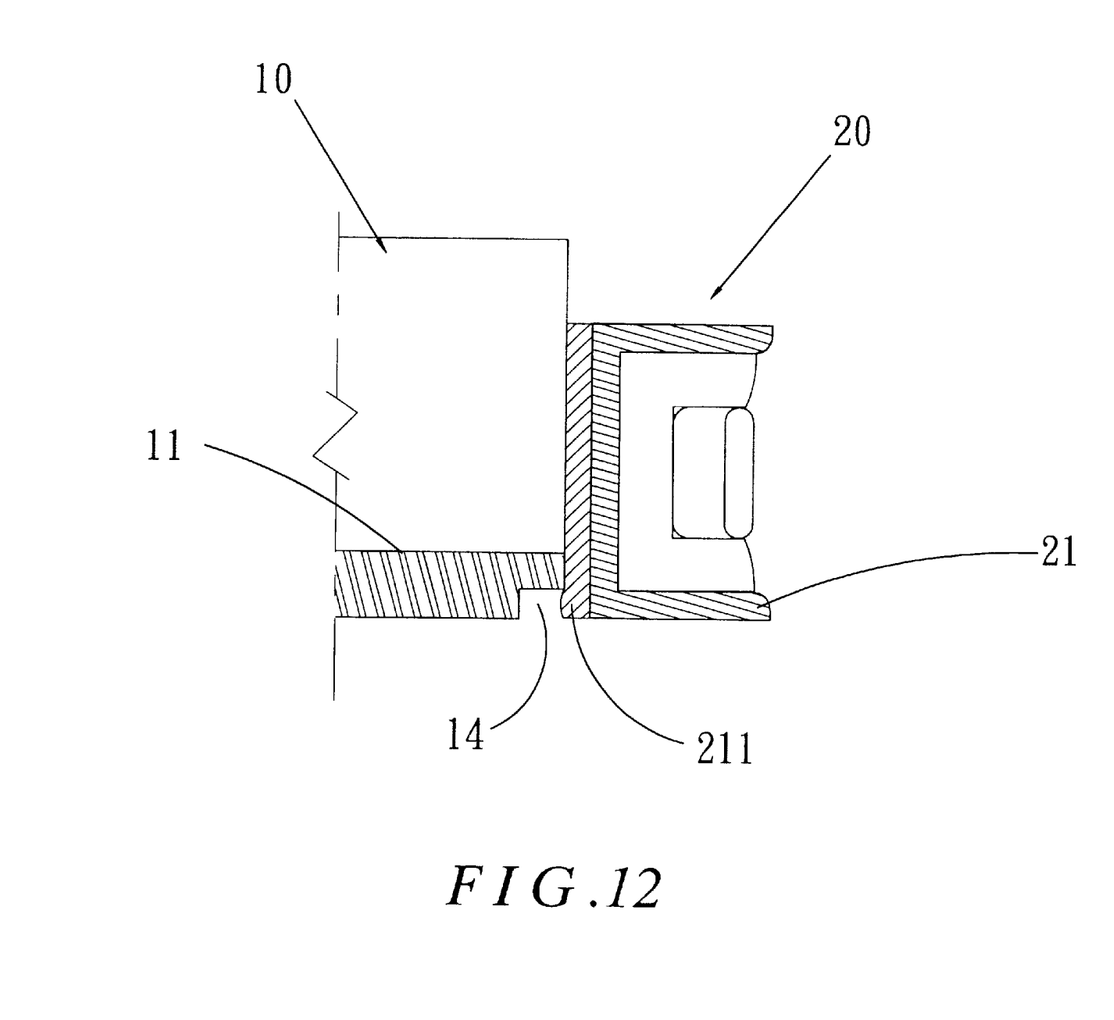
FIG. 12 is a side sectional view showing completing of assembling of the tray body and the stop members of the gel tray of the present invention.

And more, in practicing the present invention and in order to make abutment of the leakage-proof cushions 211 against the tray body 10 more tight, the bottom areas of the front and rear ends of the tray body 10 in contacting with the leakage-proof cushions 211 can be provided with recessed portions 14 (as shown in FIG. 12). When the leakage-proof cushions 211 which are made of rubber are abutted tightly against the front and rear ends of the tray body 10, the lower portions of the leakage-proof cushions 211 will be extruded to protrude slightly (as shown in FIG. 12 too). In this way, the leakage-proof cushions 211 will be abutted against the tray body 10 more tight to prevent the liquid gel cast in the tray body 10 from leaking out.

Figure 13:
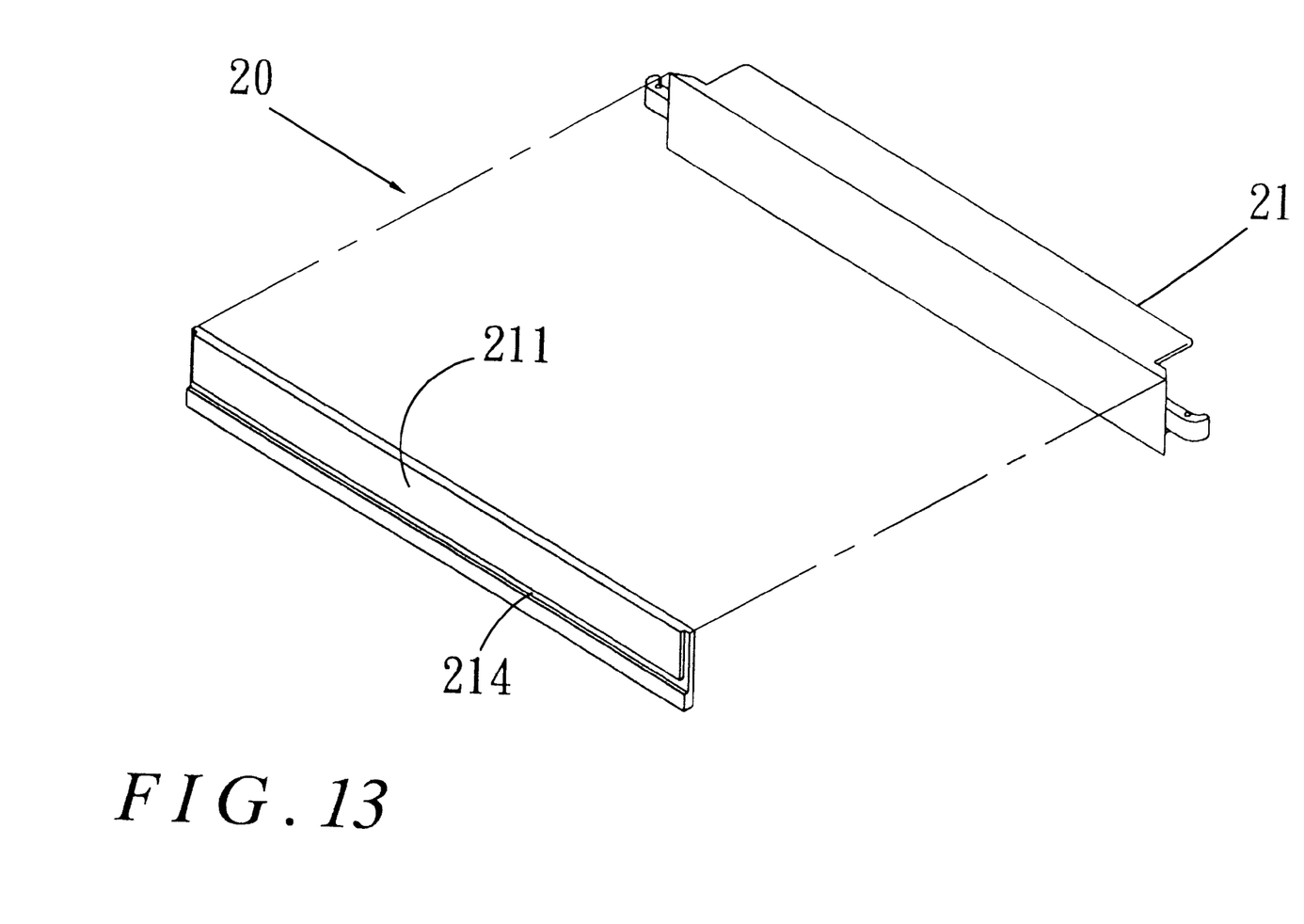
FIG. 13 shows another embodiment of a leakage-proof cushion of the present invention.

Further, to prevent plastic deformation of the areas of the leakage-proof cushions 211 abutting against the tray body 10 after being long used, in practice, the leakage-proof cushions 211 can leave, at the contact areas of them with the bottom plane plate 11 of the tray body 10 and the side wall-plates 12, "U" shaped slits 214 having three sides with widths equal to the thickness of the bottom plane plate 11 of the tray body 10 and the side wall-plates 12 respectively. Thereby, when in engaging of the slits 214(as shown in FIG. 13) with the tray body 10 and the side wall-plates 12, not only the leakage-proof cushions 211 can be prevented from deformation, but also an enhanced sealing effect can be obtained.

The names of the members composing the present invention and the shape shown in the drawings are only for illustrating a preferred embodiment of the present invention, and not for giving any limitation to the scope of the present invention. It will be apparent to those skilled in this art that various equivalent modifications or changes can be made to the elements of the present invention without departing from the spirit, scope and characteristic of this invention. Accordingly, all such modifications and changes also fall within the scope of the appended claims and are intended to form part of this invention.

What is claimed is:

1. A gel tray for an electrophoresis trough, comprising a tray body and a front and a rear stop member, wherein two side wall plates of said gel tray are extended vertically upwardly, said gel tray characterized in that:

said side wall-plates are provided with two recesses, said stop members are further respectively provided with a stop plate, and are respectively assembled together with engaging members provided respectively on both sides of said stop plates, when said stop plates are abutted against said front and rear ends of said tray body and said side wall-plates, said engaging members are engaged in said recesses provided on said side wall-plates, said stop plates thus tightly abut against said front and rear rends of said tray body and said side wall-plates, and the surrounding walls of said tray body are formed in a sealing state; after consolidation of liquid gel cast in said tray body, said engaging members are released from engaging of said side wall-plates.

2. A gel tray for an electrophoresis trough as claimed in claim 1, wherein said stop members are further provided each with a lever latch, said lever latch moves said engaging members to abut against said recesses in said side wall-plates.

3. A gel tray for an electrophoresis trough as claimed in claim 2, wherein said stop plates are straight and plane, and are each provided on both ends thereof with a connecting piece having a bent end, said engaging members are mounted each, with one end thereof on one of said connecting pieces and are provided on the other end thereof with a hook, and a pivot connecting seat is provided on each of said engaging members; said lever latches each having a pivot axle for connecting to one of said pivot connecting seats of said engaging members, in order that said lever latches are swivel about said pivot connecting seats, said lever latches each has a pushing panel corresponding in operation to one of said bending ends on the corresponding one of said connecting pieces; when said lever latches are moved, said pushing panels pushes said connecting pieces to make said engaging members tightly abut against said recesses.

4. A gel tray for an electrophoresis trough as claimed in claim 3, wherein, said connecting pieces are provided each on the top and bottom thereof with a protruding point, said engaging members each is provided with a notch to be clamped on one of said connecting pieces and each is further provided with a guide groove for insertion of said protruding point, said guide groove includes two sections, one is straight, the other is arciform; said guide groove slides on said protruding point to allow said connecting piece to move to and fro or in a mode of swaying in an arc.

5. A gel tray for an electrophoresis trough as claimed in claim 1, wherein, said stop plates are provided each on the inner side thereof facing to said front and rear ends of said tray body with a leakage-proof elastic rubber cushion.

6. A gel tray for an electrophoresis trough as claimed in claim 5, wherein, the bottom areas of said front and rear ends of said tray body in contacting with said leakage-proof cushions are provided with recessed portions, when said leakage-proof cushions are provided with recessed portions, when said leakage-proof cushions are abutted tightly against said front and rear ends of said tray body, the lower portions of said leakage-proof cushions are extruded to protrude slightly.

7. A gel tray for an electrophoresis trough as claimed in claim 5, wherein, said leakage-proof cushions leave, at the contact areas with a bottom plane plate of said tray body and said side wall-plates, "U" shaped slits (214) having three sides with widths equal to the thickness of said bottom plane plate of said tray body and said side wall-plates respectively; when said leakage-proof cushions tightly abut against said front and rear ends of said tray body, said slits engage with said bottom plane plate of said tray body and said side wall-plates.

* * * * *